(12) United States Patent
Kim et al.

(10) Patent No.: US 10,520,438 B2
(45) Date of Patent: Dec. 31, 2019

(54) COLLECTION OPTICS SYSTEM FOR SPECTROMETER AND RAMAN SPECTRAL SYSTEM

(71) Applicant: SAMSUNG ELECTRONICS CO., LTD., Suwon-si (KR)

(72) Inventors: Unjeong Kim, Osan-si (KR); Jinyoung Park, Hwaseong-si (KR); Sungmo Ahn, Yongin-si (KR); Younggeun Roh, Seoul (KR); Hongseok Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/034,609

(22) Filed: Jul. 13, 2018

(65) Prior Publication Data

US 2019/0064072 A1 Feb. 28, 2019

Related U.S. Application Data

(60) Provisional application No. 62/551,954, filed on Aug. 30, 2017.

(30) Foreign Application Priority Data

Nov. 10, 2017 (KR) .......................... 10-2017-0149792

(51) Int. Cl.
*G01N 21/65* (2006.01)
*G01J 3/44* (2006.01)
(Continued)

(52) U.S. Cl.
CPC ........... *G01N 21/65* (2013.01); *A61B 5/0075* (2013.01); *A61B 5/14532* (2013.01);
(Continued)

(58) Field of Classification Search
CPC .......... A61B 5/00; G01N 21/65; G01N 21/47; G01N 33/49; G01N 33/66;
(Continued)

(56) References Cited

U.S. PATENT DOCUMENTS 7,652,763 B2 1/2010 Matousek et al.
8,054,461 B2 11/2011 Kuo et al.
(Continued)

FOREIGN PATENT DOCUMENTS

KR 10-1139401 B1 4/2012

OTHER PUBLICATIONS

Morris, Michael D. "Ultrasensitive Raman and fluorescence imaging using liquid crystal tunable filters." Advanced Optical Methods for Ultrasensitive Detection. vol. 2385. International Society for Optics and Photonics, 1995 (Year: 1995).*

(Continued)

*Primary Examiner* — Dominic J Bologna
(74) *Attorney, Agent, or Firm* — Sughrue Mion, PLLC

(57) ABSTRACT

A collection optics system for a spectrometer and a Raman spectral system including the collection optics system is provided. The collection optics system is configured to selectively collect a Raman signal from scattered light output from a target object, the collection optics system includes a non-imaging collection unit configured to collect the Raman signal and output the Raman signal, the non-imaging collection unit including an entrance surface on which the scattered light is incident and an exit surface through which the Raman signal is output, and a Raman filter provided on a portion of the entrance surface of the non-imaging collection unit and configured to block the scattered light including a fluorescence signal. Therefore, (Continued)

the collection optics system may suppress reception of the fluorescence signal of the scattered light and selectively collect the Raman signal.

22 Claims, 16 Drawing Sheets

(51) Int. Cl.

| | | |
|---|---|---|
| G01J 3/02 | (2006.01) | |
| G01J 3/04 | (2006.01) | |
| G01N 33/66 | (2006.01) | |
| G01N 21/47 | (2006.01) | |
| A61B 5/00 | (2006.01) | |
| A61B 5/145 | (2006.01) | |

(52) U.S. Cl.
CPC ............... *G01J 3/0216* (2013.01); *G01J 3/04* (2013.01); *G01J 3/44* (2013.01); *G01J 3/4412* (2013.01); *G01N 21/47* (2013.01); *G01N 33/66* (2013.01); *G01J 2003/4424* (2013.01); *G01N 2021/4735* (2013.01)

(58) Field of Classification Search
CPC .. G01N 2021/4735; G01J 3/0216; G01J 3/04; G01J 3/44; G01J 3/4412; G01J 2003/4424
See application file for complete search history.

(56) References Cited

U.S. PATENT DOCUMENTS

| | | | |
|---|---|---|---|
| 8,692,990 | B2 | 4/2014 | Matousek |
| 9,662,047 | B2 | 5/2017 | Barman et al. |
| 2005/0092360 | A1 | 5/2005 | Clark |
| 2007/0129711 | A1* | 6/2007 | Altshuler ........... A45D 26/0061 606/9 |
| 2008/0051645 | A1 | 2/2008 | Rebec et al. |
| 2008/0076985 | A1 | 3/2008 | Matousek et al. |
| 2012/0035442 | A1* | 2/2012 | Barman ............. A61B 5/14532 600/316 |
| 2013/0265568 | A1* | 10/2013 | Micheels ............. G01N 21/359 356/51 |
| 2014/0252232 | A1* | 9/2014 | Reinke ................... G01N 21/55 250/338.1 |
| 2015/0247795 | A1* | 9/2015 | Hruska ................ G01N 21/359 250/339.02 |
| 2016/0123869 | A1* | 5/2016 | Messerschmidt .... A61B 5/0075 356/39 |
| 2016/0258814 | A1 | 9/2016 | Cho et al. |
| 2016/0356720 | A1* | 12/2016 | Van Dorpe .......... A61B 5/0066 |
| 2017/0100064 | A1 | 4/2017 | Van Dorpe et al. |

OTHER PUBLICATIONS

Duffie, et al., "Overview of Concentrating Collectors", 2015, EME 811: Solar Thermal Energy for Utilities and Industry, 3 pages total.
Conti, et al., "Comparison of key modalities of micro-scale spatially offset Raman spectroscopy", 2015, The Royal Society of Chemistry, vol. 140, pp. 8127-8133.
O'Gallagher, et al., "Axially symmetric nonimaging flux concentrators with the maximum theoretical concentration ratio", 1987, Journal of the Optical Society of America, vol. 4, Issue No. 1, pp. 66-68.
Sekar, et al., "Frequency offset Raman spectroscopy (FORS) for depth probing of diffusive media", 2017, Optics Express, vol. 25, Issue No. 5, pp. 4585-4597.
Kazunori Tanaka et al., "Compound parabolic concentrator probe for efficient light collection in spectroscopy of biological tissue", Applied Optics, Optical Society of America, vol. 35, No. 4, Feb. 1, 1996, pp. 758-763, XP000630308. (6 pages total).
Search Report dated Feb. 11, 2019 by the European Patent Office in counterpart European Patent Application No. 18191112.4.

* cited by examiner

COLLECTION OPTICS SYSTEM FOR SPECTROMETER AND RAMAN SPECTRAL SYSTEM

CROSS-REFERENCE TO RELATED APPLICATIONS

This application claims priority from U.S. Provisional Application No. 62/551,954, filed on Aug. 30, 2017 in the U.S. Patent and Trademark Office and Korean Patent Application No. 10-2017-0149792, filed on Nov. 10, 2017 in the Korean Intellectual Property Office, the disclosures of which are incorporated herein in their entireties by reference.

BACKGROUND

1. Field

Example embodiment of the present disclosure relate to a spectrometer, and more particularly, to a collection optics system for a spectrometer, and a Raman spectral system including the collection optics system.

2. Description of the Related Art

Recently, smaller Raman spectral systems for analyzing substances in the body such as blood glucose have been developed as diagnosis sensors for mobile health. Technology for examining body samples such as a skin sample using such smaller Raman spectral systems may bring improvements in aspects such as the range of measurement or the possible number of measurements, compared to existing technology enabling measurements only at particular positions or in particular regions. However, since the body produces intensive fluorescence signals, technology for selectively detecting only Raman signals from biogenic substances existing in very small amounts such as blood glucose is needed.

SUMMARY

Provided are collection optics systems for spectrometers, and Raman spectral systems including the collection optics systems.

According to an aspect of an example embodiment, there is provided a collection optics system for a spectrometer, the collection optics system being configured to selectively collect a Raman signal from scattered light output from a target object, the collection optics system including a non-imaging collection unit configured to collect the Raman signal from the scattered light and output the Raman signal, the non-imaging collection unit including an entrance surface on which the scattered light is incident and an exit surface through which the Raman signal is output, and a Raman filter provided on a portion of the entrance surface of the non-imaging collection unit and configured to block a portion of the scattered light including a fluorescence signal.

The target object may include a material having turbidity and may output the scattered light including the fluorescence signal and the Raman signal based on light incident on the target object from a light source.

The target object may include human skin, and the Raman signal may include a blood glucose Raman signal.

The Raman filter may be provided on a center portion of the entrance surface of the non-imaging collection unit, the center portion being a portion on which the fluorescence signal is incident.

The size of the entrance surface of the non-imaging collection unit may be equal to or less than 1 cm.

The size of the Raman filter may be equal to or less than 1 mm.

The Raman filter may be further configured to transmit the light incident on the target object in an incident-light wavelength band and configured to block the scattered light output from the target object in a scattered-light wavelength band.

The Raman filter may be further configured to transmit the light incident in a wavelength band.

The Raman filter may include a plurality of wavelength filters configured to transmit the light incident in a plurality of wavelength bands.

The plurality of wavelength filters may be provided in a grid form or concentric ring form.

A transparent member configured to transmit the scattered light containing the Raman signal or a band filter configured to transmit a predetermined Raman wavelength may be provided on the entrance surface of the non-imaging collection unit around the Raman filter.

The non-imaging collection unit may further include an elliptical hyperboloid concentrator, a circular hyperboloid concentrator, a circular cone concentrator, an elliptical cone concentrator, or a compound parabolic concentrator.

The area of the entrance surface of the non-imaging collection unit may be smaller than an area of the exit surface of the non-imaging collection unit.

The area of the entrance surface of the non-imaging collection unit may be larger than an area of the exit surface of the non-imaging collection unit.

According to an aspect of an example embodiment, there is provided a Raman spectral system including a light source configured to emit light to a target object, a collection optics system configured to selectively collect a Raman signal from scattered light output from the target object based on the light incident from the light source and output the Raman signal, and a spectrometer configured to receive the Raman signal output from the collection optics system, wherein the collection optics system includes a non-imaging collection unit configured to collect the Raman signal from the scattered light and output the Raman signal, the non-imaging collection unit including an entrance surface on which the scattered light is incident and an exit surface through which the Raman signal is output, and a Raman filter provided on a portion of the entrance surface of the non-imaging collection unit and configured to block a portion of the scattered light including a fluorescence signal.

The Raman filter may be provided on a center portion of the entrance surface of the non-imaging collection unit, the center portion being a portion on which the fluorescence signal is incident.

The Raman filter may be further configured to transmit the light incident on the target object in an incident-light wavelength band and configured to block the scattered light output from the target object in a scattered-light wavelength band.

A transparent member configured to transmit the scattered light including the Raman signal or a band filter configured to transmit a predetermined Raman wavelength may be provided on the entrance surface of the non-imaging collection unit around the Raman filter.

The non-imaging collection unit may further include an elliptical hyperboloid concentrator, a circular hyperboloid concentrator, a circular cone concentrator, an elliptical cone concentrator, or a compound parabolic concentrator.

The light emitted from the light source may be incident on a surface of the target object at right angle or an oblique angle.

The spectrometer may include an on-chip spectrometer.

The spectrometer may include a dispersive-type spectrometer including a slit configured to receive the Raman signal, and wherein the exit surface of the non-imaging collection unit is inserted in the slit.

According to an aspect of an example embodiment, there is provided a Raman spectral system including a light source configured to emit light to a target object, a collection optics system including a non-imaging collection unit comprising an entrance surface configured to collect the Raman signal included in a scattered light output from the target object based on the light emitted from the light source, and an exit surface configured to output the collected Raman signal, and a Raman filter provided on a center portion of the entrance surface of the non-imaging collection unit and configured to block a fluorescence signal included in the scattered light, and a spectrometer configured to receive the Raman signal output from the collection optics system.

The Raman filter may include a plurality of wavelength filters configured to transmit the light emitted on the target objection in a plurality of wavelength bands, the plurality of wavelength filters being provided in a grid form or concentric ring form.

The non-imaging collection unit may further include a transparent member configured to transmit the scattered light containing the Raman signal or a band filter configured to transmit a predetermined Raman wavelength, wherein the transparent member or the band filter is provided on the entrance surface of the non-imaging collection unit around the Raman filter.

The non-imaging collection unit may further include an elliptical hyperboloid concentrator, a circular hyperboloid concentrator, a circular cone concentrator, an elliptical cone concentrator, or a compound parabolic concentrator

BRIEF DESCRIPTION OF THE DRAWINGS

These and/or other aspects will become apparent and more readily appreciated from the following description of the example embodiments, taken in conjunction with the accompanying drawings in which.

DETAILED DESCRIPTION

Figure 1:
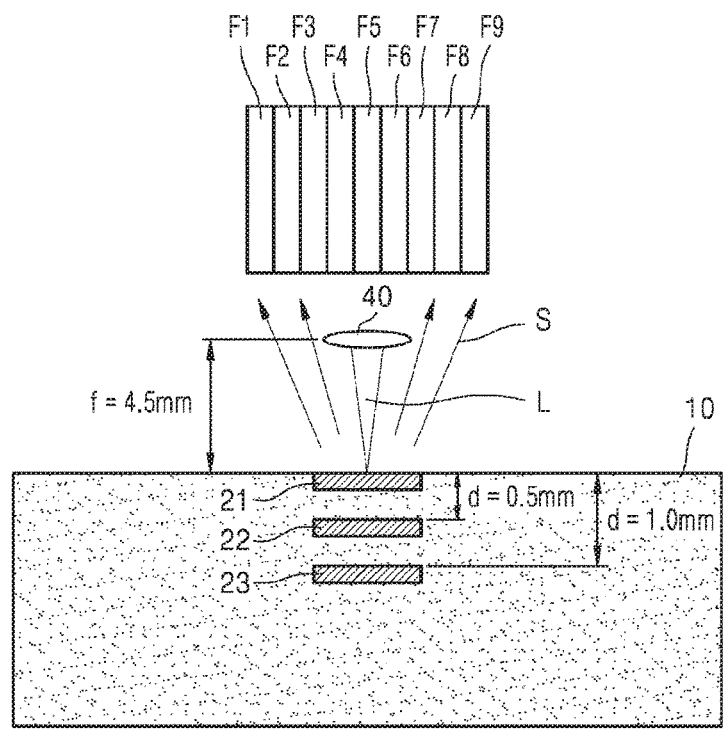
FIG. 1 is a view illustrating measurement of scattered light output from a test sample by using fibers when the test sample is irradiated with laser light according to an example embodiment.

Reference will now be made in detail to example embodiments, of which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects.

As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

As used herein, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the drawings, the size of each element may be exaggerated for clarity of illustration. In addition, when a material layer is referred to as being "above" or "on" a substrate or another layer, it can be directly on the substrate or the other layer, or intervening layers may also be present. In the following description, a material of each layer is an example. That is, another material may be used.

It will be understood that, although the terms "first," "second," "third," etc., may be used herein to describe various elements, elements are not limited by these terms. These terms are only used to distinguish one element from another element.

The skin is a medium having turbidity compared to general reflective media. Turbidity may be expressed by a scattering coefficient and a reduced scattering coefficient provided by considering an anisotropic factor which is one of the properties of the skin. The reduced scattering coefficient of the skin may range from about 1 $mm^{-1}$ to about 3 $mm^{-1}$. In general, the spreading of Raman signals from a medium having turbidity is much wider than the spreading of Raman signals from a reflective medium. In addition, because of fluorescence signals output from the epidermis existing from the surface of the skin to a depth of about 100 μm to about 400 μm, it is difficult to detect Raman signals coming from blood glucose intensively existing in the dermis or to detect other signals.

Figure 2:
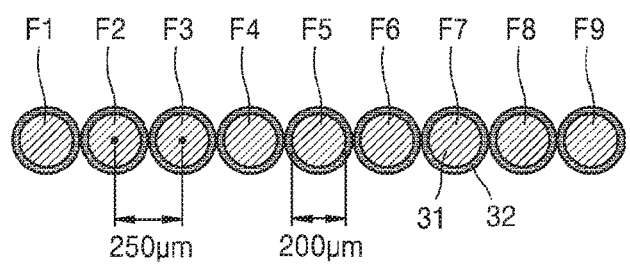
FIG. 2 is a cross-sectional view illustrating the fibers illustrated in FIG. 1.

FIG. 1 illustrates measurement of scattered light output from a test sample 10 having turbidity by using fibers when the test sample 10 is irradiated with light. FIG. 2 is a cross-sectional view illustrating the fibers illustrated in FIG. 1. For example, a medium having a scattering coefficient range of normal skin may be used as the test sample 10 for measurement. The scattering coefficient and reduced scattering coefficient of the test sample 10 may be respectively 2.4 $mm^{-1}$ and 1.13 $mm^{-1}$ at a wavelength of 755 nm. A laser beam having a wavelength of 785 nm may be radiated on the test sample 10 as incident light L.

Figure 3:
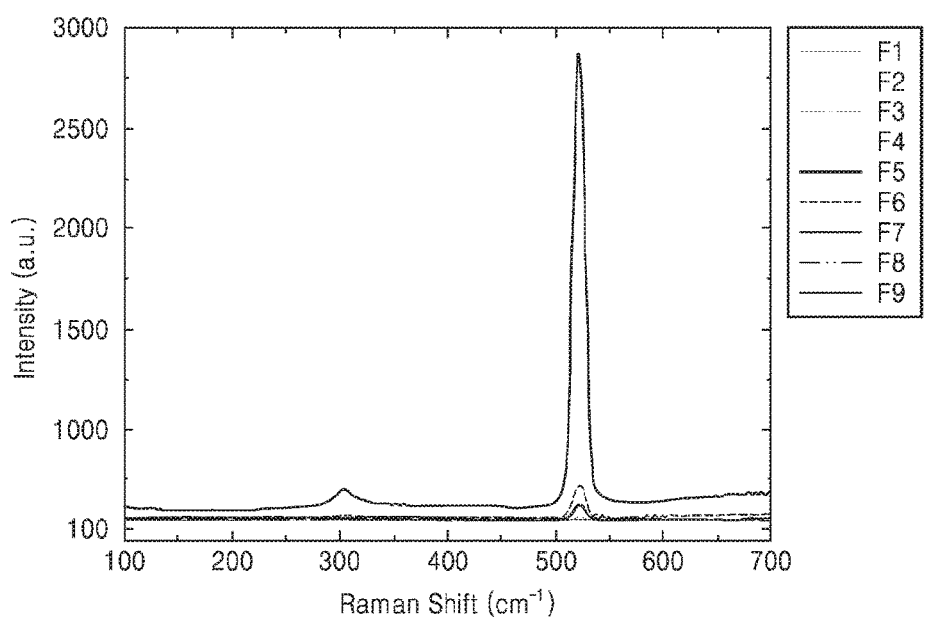
FIG. 3 is a graph illustrating Raman spectrums collected by the fibers from scattered light output from a first silicon substrate shown in FIG. 1.

Referring to FIG. 1, according to an example embodiment, a first silicon substrate 21, a second silicon substrate 22, and a third silicon substrate 23 are placed in the test sample 10 in a depth direction from a surface of the test sample 10. Here, the first silicon substrate 21 may be placed on the surface of the test sample 10. In addition, the second silicon substrate 22 may be placed at a depth d of 0.5 mm from the surface of the test sample 10, and the third silicon substrate 23 may be placed at a depth d of 1.0 mm from the surface of the test sample 10. That is, the medium having turbidity may not be placed above the first silicon substrate 21, but the medium having turbidity may be placed above the second and third silicon substrates 22 and 23. A laser beam emitted from a light source may be radiated upon the test sample 10 as incident light L, and scattered light S output from the test sample 10 may be collected by a fiber bundle provided above the test sample 10. For example, the laser beam may be condensed by a focusing lens 40 and may be radiated as incident light L upon each of the first silicon substrate 21, the second silicon substrate 22, and the third silicon substrate 23. Here, a distance f from the focusing lens 40 to the surface of the test sample 10 may be 4.5 mm. Upon being irradiated by the incident light L, scattered light S containing Raman signals may be output from each of the first to third silicon substrates 21 to 23, and the scattered light S may be collected by nine fibers F1 to F9 arranged in a line above the test sample 10. The fibers F1 to F9 may be arranged such that the fifth fiber F5 located at the center of the fibers F1 to F9 may be at a position corresponding to the center of the scattered light S. Referring to FIG. 2, each of the fibers F1 to F9 may include a core 31 and a clad layer 32 enclosing the core 31. According to an example embodiment, the diameter of the cores 31 of the nine fibers F1 to F9 may be 200 μm, and the nine fibers F1 to F9 may be arranged at intervals of 250 μm. FIG. 3 illustrates Raman spectrums collected by the fibers F1 to F9 from scattered light output from the first silicon substrate 21 shown in FIG. 1. FIG. 3 illustrates Raman spectrums collected by the nine fibers F1 to F9 from scattered light S output from the first silicon substrate 21 after a laser beam is incident on the first silicon substrate 21 as incident light L.

Referring to FIG. 3, it may be understood that the Raman signals of the scattered light S output from the first silicon substrate 21, on which the medium having turbidity is not placed because the first silicon substrate 21 is disposed on the surface of the test sample 10, are mostly collected by the fifth fiber F5 located at the center of the fibers F1 to F9.

Figure 4A:
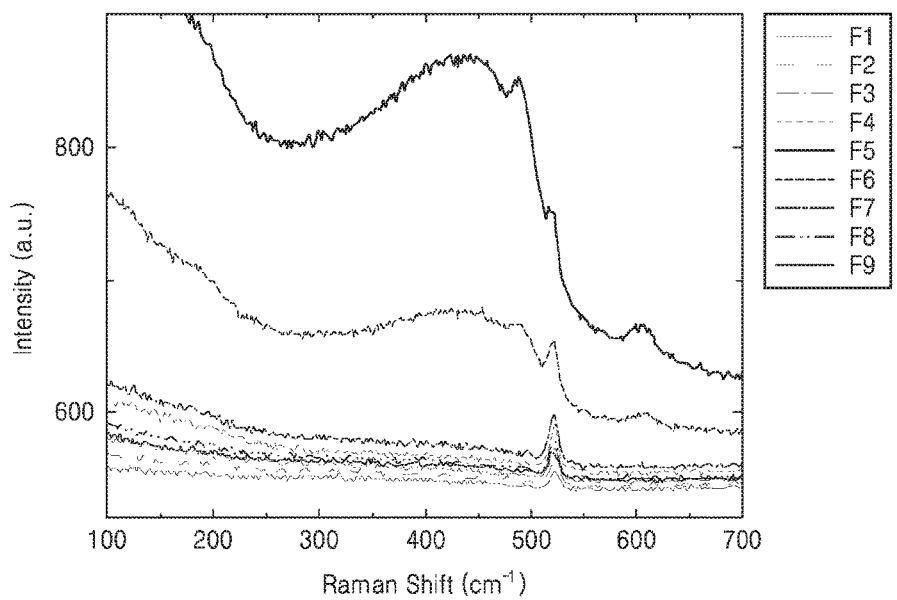
FIG. 4A is a graph illustrating Raman spectrums collected by the fibers from scattered light output from a second silicon substrate shown in FIG. 1.
Figure 4B:
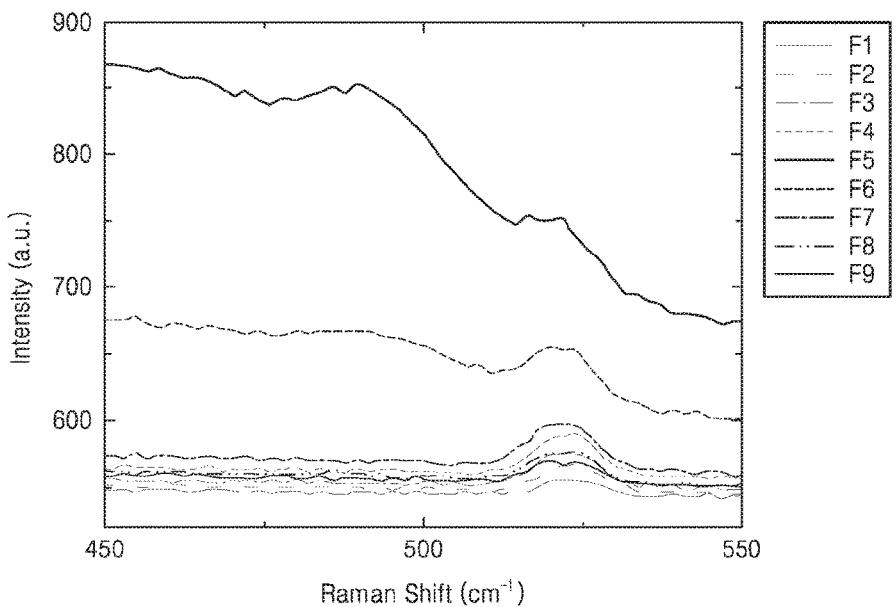
FIG. 4B is an enlarged view of the Raman spectrums shown in FIG. 4A.

FIG. 4A illustrates Raman spectrums collected by the fibers F1 to F9 from scattered light output from the second silicon substrate 22 shown in FIG. 1. FIG. 4B is an enlarged view of the Raman spectrums shown in FIG. 4A. FIGS. 4A and 4B illustrate Raman spectrums collected by the nine fibers F1 to F9 from scattered light S output from the second silicon substrate 22 after a laser beam is incident as incident light L on the second silicon substrate 22 placed at a depth d of 0.5 mm from the surface of the test sample 10 having turbidity similar to turbidity of the human skin.

Figure 5A:
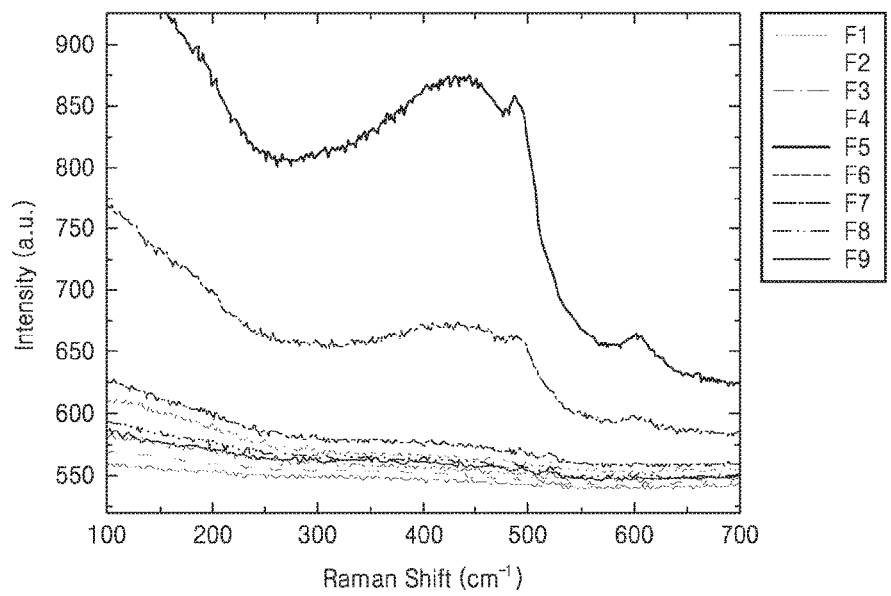
FIG. 5A is a graph illustrating Raman spectrums collected by the fibers from scattered light output from a third silicon substrate shown in FIG. 1.
Figure 5B:
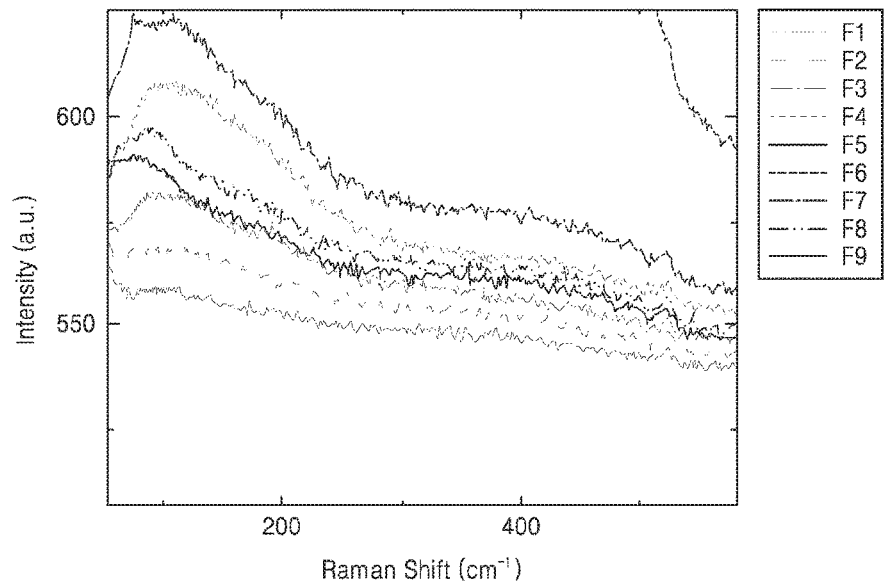
FIG. 5B is an enlarged view of the Raman spectrums shown in FIG. 5A.

FIG. 5A illustrates Raman spectrums collected by the fibers F1 to F9 from scattered light output from the third silicon substrate 23 shown in FIG. 1. FIG. 5B is an enlarged view of the Raman spectrums shown in FIG. 5A. FIGS. 5A and 5B illustrate Raman spectrums collected by the nine fibers F1 to F9 from scattered light S output from the third silicon substrate 23 after a laser beam is incident as incident light L on the third silicon substrate 23 placed at a depth d of 1.0 mm from the surface of the test sample 10.

Referring to FIGS. 4A, 4B, 5A, and 5B illustrate that signals of scattered light from the second silicon substrate 22 or the third silicon substrate 23 on which a medium having turbidity is placed may be more widely dispersed and collected by the nine fibers F1 to F9 compared to scattered light from the first silicon substrate 21 without a medium having turbidity being placed. Furthermore, FIGS. 4A, 4B, 5A, and 5B illustrate that in a direction away from the fifth fiber F5 located at the center of the fibers F1 to F9, the intensity of fluorescence signals is weakened, and Raman signals are observed.

Figure 6:
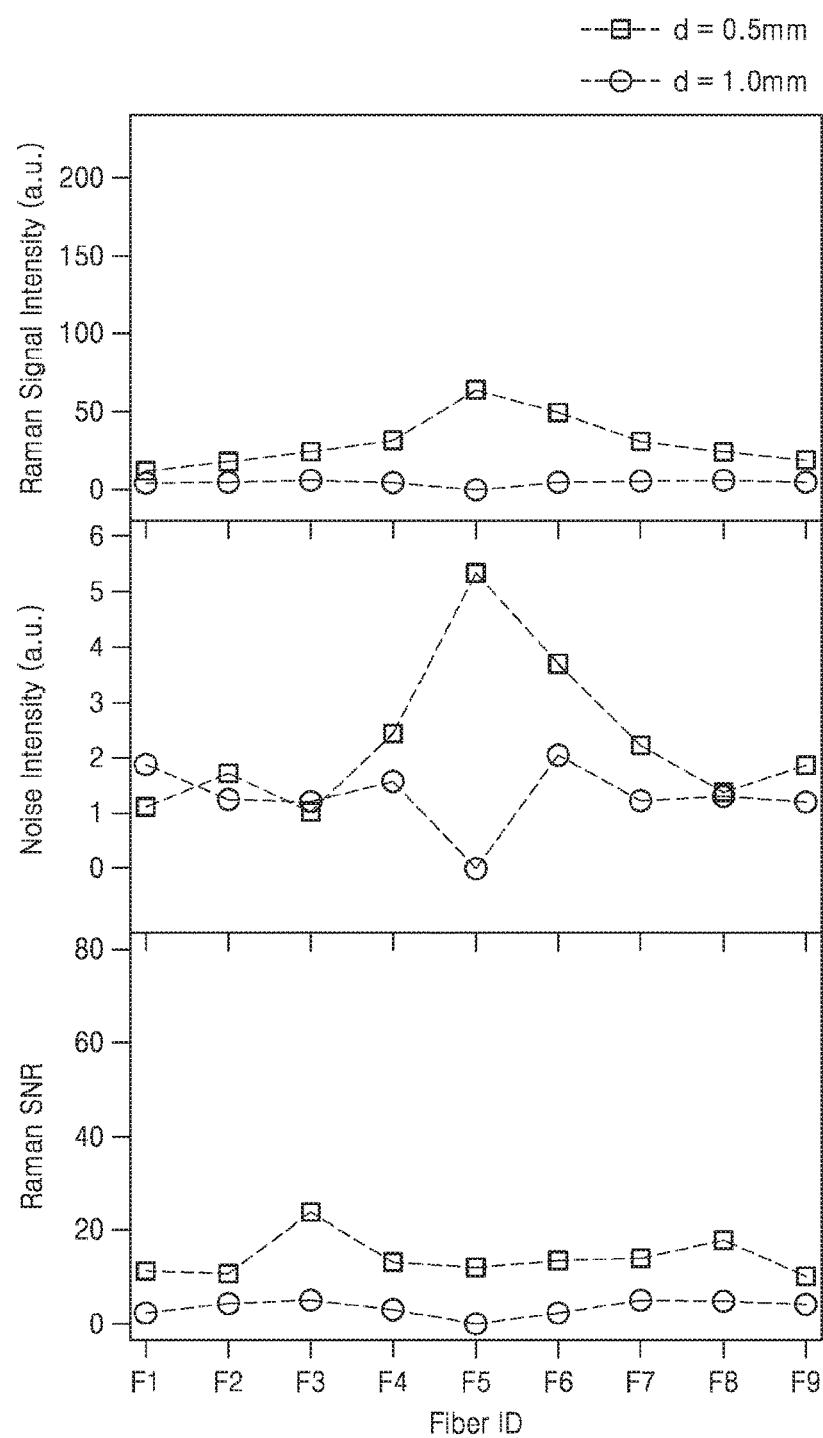
FIG. 6 is a graph illustrating Raman signals, pieces of noise, and a calculated Raman signal to noise ratio (SNR) according to the positions of the fibers in FIGS. 4A to 5B.

FIG. 6 illustrates Raman signals, noise, and a calculated Raman signal to noise ratio (SNR) in the Raman spectrums shown in FIGS. 4A to 5B, according to the positions of the fibers F1 to F9.

Referring to FIG. 6, the noise may include, for example, readout noise, shot noise, and systematic noise, and if there is a strong fluorescence signal, the shot noise may account for most of the noise. Therefore, if the fluorescence signal is selectively reduced, the shot noise may decrease, and thus, the SNR may be improved. In addition, although the Raman signal decreases at the fifth fiber F5 located at the center of the fibers F1 to F9, as the fluorescence signal also decreases, the noise decreases. Thus, the SNR may increase at a position spaced apart from the fifth fiber F5 by a distance of 0.5 mm.

Figure 7A:
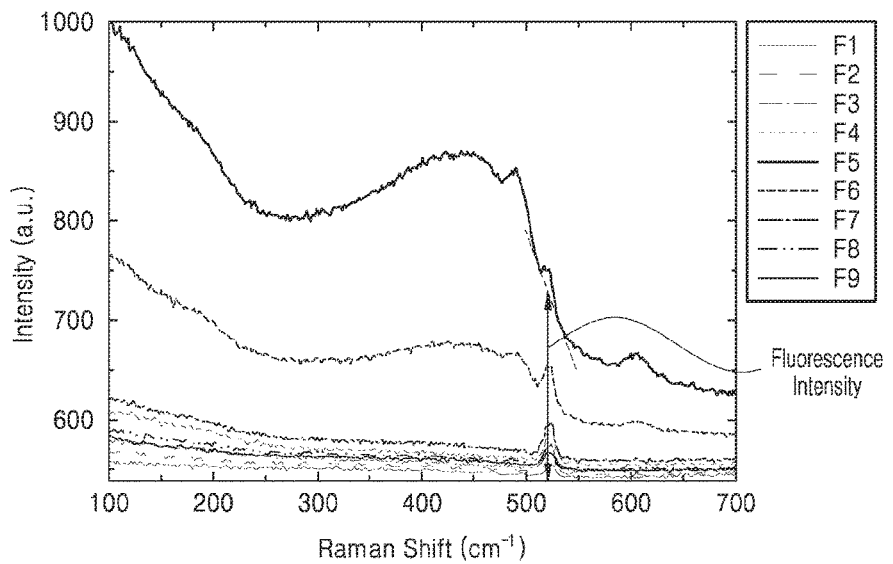
FIG. 7A is a graph illustrating Raman spectrums collected by the fibers from scattered light output from a test sample having turbidity of the skin.
Figure 7B:
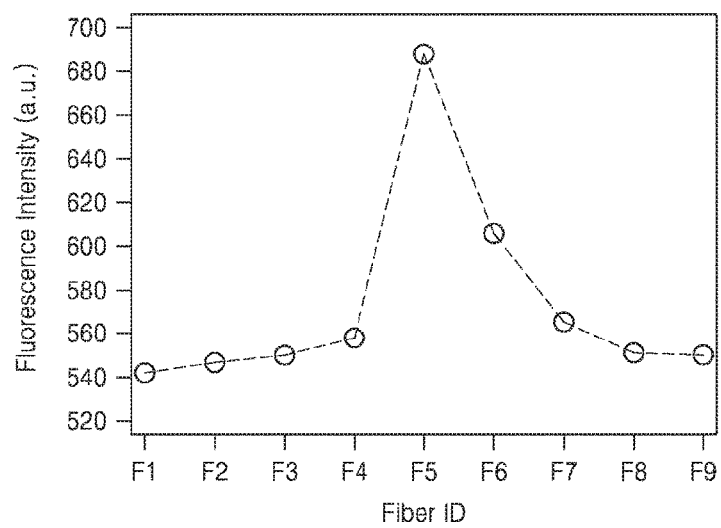
FIG. 7B is a graph illustrating fluorescence signal intensity calculated from the Raman spectrums shown in FIG. 7A.

FIG. 7A illustrates Raman spectrums collected by the fibers F1 to F9 from scattered light output from a test sample having turbidity similar to turbidity of the skin. FIG. 7B illustrates fluorescence signal intensity calculated from the Raman spectrums shown in FIG. 7A. The fluorescence signal intensity shown in FIG. 7B is defined by the size of a portion under a peak of interest as shown in FIG. 7A. Referring to FIGS. 7A and 7B, the fluorescence signal intensity sharply decreases in a direction from the fifth fiber F5 located at the center of the fibers F1 to F9 toward an outermost fiber, the first or ninth fiber F1 or F9.

Figure 8A:
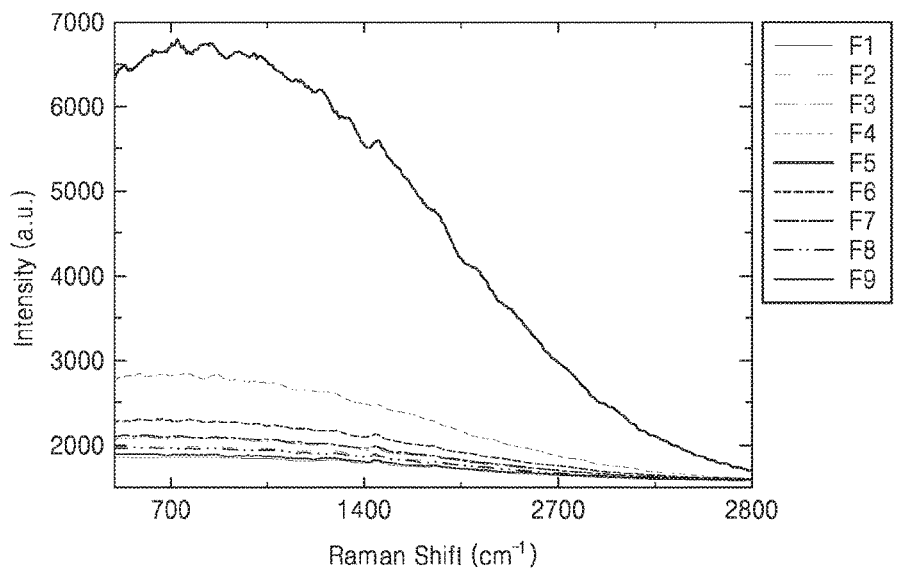
FIG. 8A is a graph illustrating Raman spectrums collected by the fibers from scattered light output from real skin.
Figure 8B:
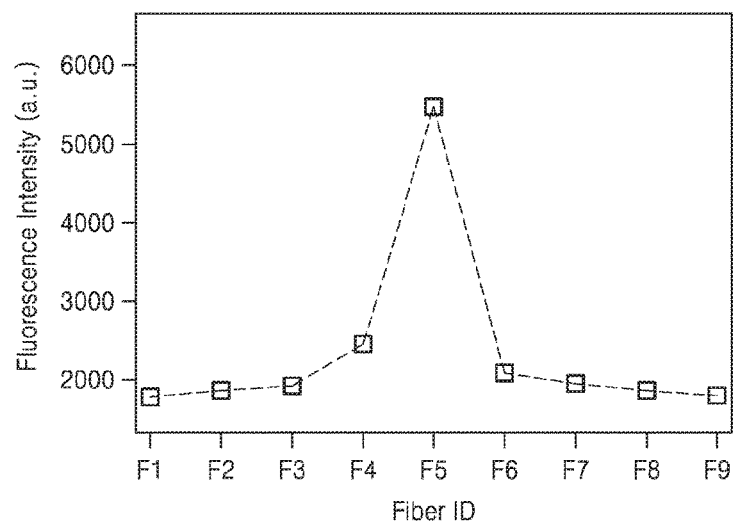
FIG. 8B is a graph illustrating fluorescence signal intensity in the Raman spectrums shown in FIG. 8A.
Figure 8C:
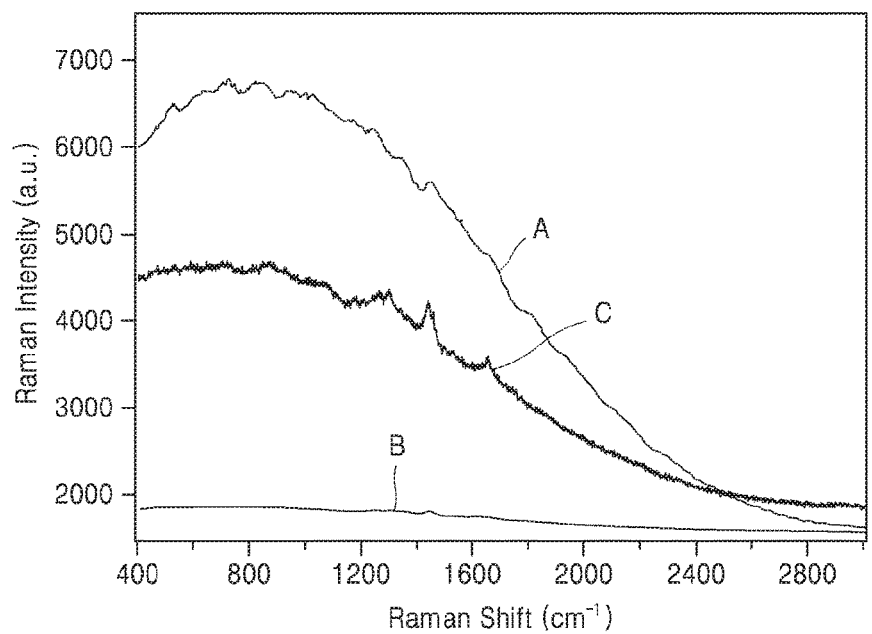
FIG. 8C is a graph illustrating Raman signal intensity in the Raman spectrums shown in FIG. 8A.

FIG. 8A illustrates Raman spectrums collected by the fibers F1 to F9 from scattered light output from human skin. FIG. 8B illustrates fluorescence signal intensity in the Raman spectrums shown in FIG. 8A. FIG. 8C illustrates Raman signal intensity in the Raman spectrums shown in FIG. 8A. In FIG. 8C, A denotes a Raman signal collected by the fifth fiber F5 located at the center of the fibers F1 to F9, and B denotes a Raman signal collected by an outermost fiber, the first or ninth fiber F1 or F9. In addition, C shows the Raman signal B at a magnification of 10 times.

Referring to FIGS. 8A to 8C, the fluorescence signal intensity sharply decreases in a direction from the fifth fiber F5 located at the center of the fibers F1 to F9 toward an outermost fiber, the first or ninth fiber F1 or F9. For example, the intensity of a fluorescence signal collected by the outermost fiber, the first or ninth fiber F1 or F9, is about 1/3 of the intensity of a fluorescence signal collected by the fifth fiber F5. In addition, as illustrated in FIG. 8C, as the fluorescence signal intensity decreases, the resolution of Raman peaks improves.

As described above, when a laser beam is radiated as incident light L upon the test sample 10 including a material having the same turbidity as the human skin, the test sample 10 emits scattered light S in response to the incident light L, and the scattered light S contains a Raman signal and a fluorescence signal hindering the reception of the Raman signal. However, since most of the fluorescence signal is included in a center portion of the scattered light S output from the test sample 10, if the center portion of the scattered light S is blocked, the Raman signal may be selectively collected.

Figure 9:
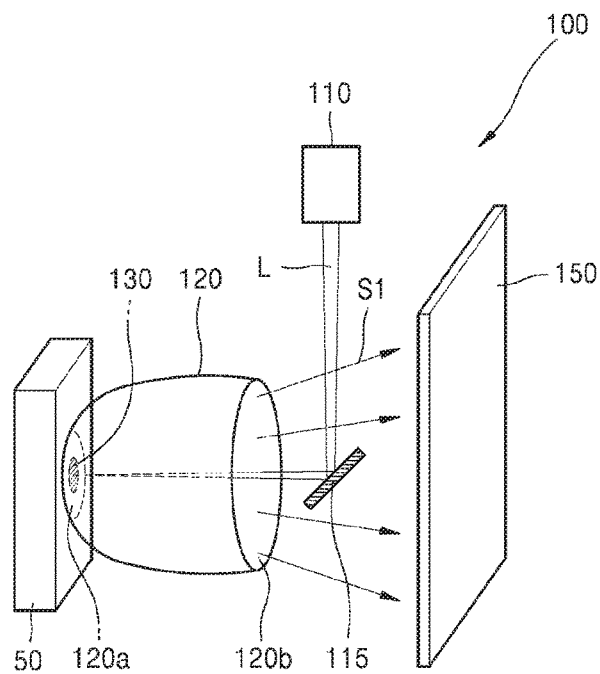
FIG. 9 is a perspective view illustrating a Raman spectral system according to an example embodiment.

FIG. 9 illustrates a Raman spectral system 100 according to an example embodiment.

Referring to FIG. 9, the Raman spectral system 100 may include a light source 110 configured to emit light L toward an target object 50, a collection optics system configured to selectively collect Raman signals S1 from scattered light output from the target object 50, and a spectrometer 150 configured to receive the collected Raman signals S1 from the collection optics system. Here, the target object 50 may include a material having a certain degree of turbidity. For example, the target object 50 may include the skin of a human. However, examples of the target object 50 are not limited thereto.

The light source 110 may emit light L toward the target object 50. For example, the light source 110 may emit a laser beam having a wavelength of 785 nm as light L. Light L emitted from the light source 110 may be reflected by a refection mirror 115 toward a test region of the target object 50. Herein, a focusing lens may be provided in an optical path of the light L to focus the light L. The light L may reach the test region of the target object 50 after passing through a Raman filter 130 provided on an entrance surface 120a of a non-imaging collection unit 120. The light L may be perpendicularly incident on a surface the target object 50.

As the light L is incident on the test region of the target object 50 from the light source 110, the test region of the target object 50 may output scattered light. In this case, since the target object 50 has turbidity, the scattered light output from the target object 50 contains Raman signals S1 and also fluorescence signals S2 that hinder reception of the Raman signals S1.

The collection optics system may selectively collect the Raman signals S1 from the scattered light output from the target object 50. According to an example embodiment, collection optics system may include the non-imaging collection unit 120 and the Raman filter 130.

Figure 10:
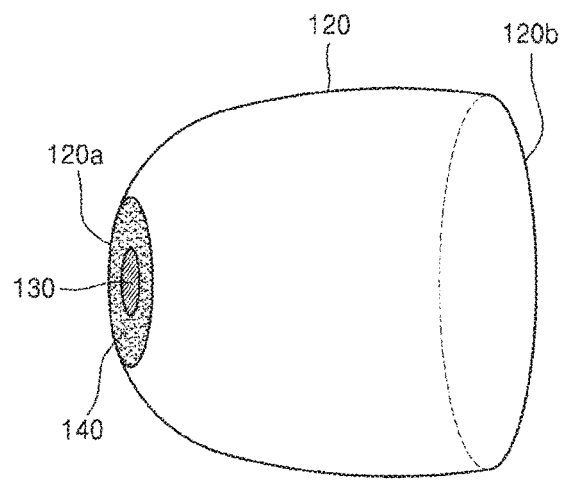
FIG. 10 is an enlarged perspective view illustrating a non-imaging collection unit illustrated in FIG. 9.

FIG. 10 is an enlarged perspective view illustrating the non-imaging collection unit 120 illustrated in FIG. 9. In addition, FIG. 11 is a view illustrating the entrance surface 120a of the non-imaging collection unit 120 illustrated in FIG. 10.

Figure 11:
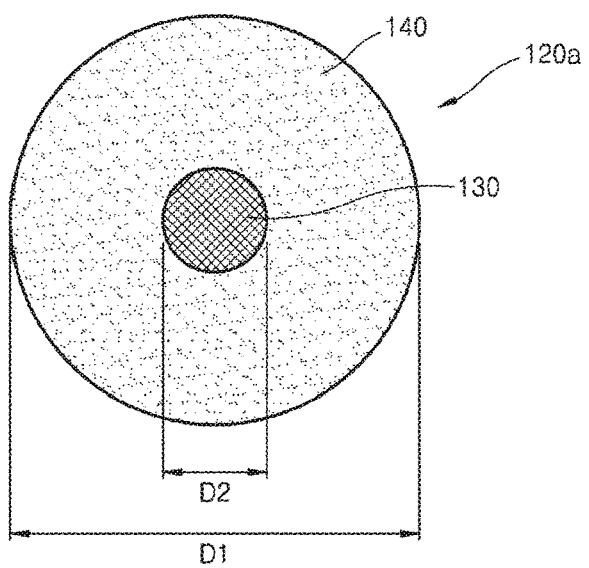
FIG. 11 is a view illustrating an entrance surface of the non-imaging collection unit illustrated in FIG. 10.

Referring to FIGS. 10 and 11, the non-imaging collection unit 120 may be used to collect scattered light output from the target object 50. The non-imaging collection unit 120 is a collection system using no lens and configured to optimally deliver light from a point in which light is generated to a destination. Application fields of the non-imaging collection unit 120 include, for example, solar cells and illumination. For example, in the field of solar cells, the non-imaging collection unit 120 may be used to increase or maximize the amount of solar energy that is transferred to a solar cell from a solar energy concentrator.

FIG. 10 illustrates an example in which a compound parabolic concentrator (CPC) is used as the non-imaging collection unit 120. The non-imaging collection unit 120 may include the entrance surface 120a on which scattered light output from the target object 50 is incident, and an exit surface 120b located opposite the entrance surface 120a and through which Raman signals S1 are output.

The entrance surface 120a of the non-imaging collection unit 120 may have an area smaller than that of the exit surface 120b. In the case in which the entrance surface 120a of the non-imaging collection unit 120 is brought into contact with the target object 50 for performing a measurement operation, the entrance surface 120a of the non-imaging collection unit 120 may have a diameter D1 of, for example, about 1 cm. However, example embodiments of the entrance surface 120a are not limited thereto.

The Raman filter 130 is provided on a portion of the entrance surface 120a of the non-imaging collection unit 120 to reduce or block fluorescence signals S2. That is, the Raman filter 130 may have a function of blocking fluorescence signals S2 included in scattered light output from the target object 50.

As described above, most of the fluorescence signals S2 included in scattered light output from the target object 50 having turbidity are in a center portion of the scattered light. Therefore, the Raman filter 130 may be provided on a portion of the entrance surface 120a of the non-imaging collection unit 120 on which most fluorescence signals S2 are incident, that is, on a center portion of the entrance surface 120a, to suppress the reception of fluorescence signals S2 output from the target object 50. In addition, a transparent member 140 may be further provided on the entrance surface 120a of the non-imaging collection unit 120 in a region around the Raman filter 130. The transparent member 140 may transmit scattered light output from the target object 50 and may support the Raman filter 130. In addition, a band filter configured to transmit a particular Raman wavelength may be provided on the entrance surface 120a of the non-imaging collection unit 120 around the Raman filter 130.

FIGS. 10 and 11 illustrate an example in which the Raman filter 130 provided on the center portion of the entrance surface 120a of the non-imaging collection unit 120 has a circular shape. In the case in which the entrance surface 120a of the non-imaging collection unit 120 is brought into contact with the target object 50 for performing a measurement operation, the Raman filter 130 may have a diameter D2 of about 1 mm. However, example embodiments of the Raman filter 130 are not limited thereto.

The Raman filter 130 may transmit light L incident on the target object 50 from the light source 110 in an incident-light wavelength band and may block scattered light output from the target object 50 in a scattered-light wavelength band.

That is, when light L is incident on the test region of the target object 50, scattered light S is output from the test region of the target object 50, and the scattered light S may be output in a wavelength band different from the wavelength band of the incident light because of a Raman shift. Therefore, the Raman filter 130 may transmit incident light L, but may block scattered light S output in a wavelength band different from the wavelength band of the incident light L.

For example, the Raman filter 130 may include a band pass filter configured to transmit light in a particular wavelength band or a short pass filter configured to transmit light having a wavelength equal to or shorter than a particular value. For example, when the Raman filter 130 includes a band pass filter, Stokes Raman signals and anti-Stokes Raman signals may be measured. In addition, when the Raman filter 130 includes a short pass filter, only Stokes Raman signals may be measured.

The Raman filter 130 may be provided on the center portion of the entrance surface 120a of the non-imaging collection unit 120. Incident light L from the target object 50 passes through the Raman filter 130 and reaches the test region of the target object 50, as shown in FIG. 9. Then, the test region of the target object 50 irradiated with the incident light L emits scattered light. Herein, a center portion of the scattered light, that is, scattered light propagating toward the center portion of the entrance surface 120a of the non-imaging collection unit 120 and containing fluorescence signals S2, may be reduced or blocked by the Raman filter 130.

Figure 12:
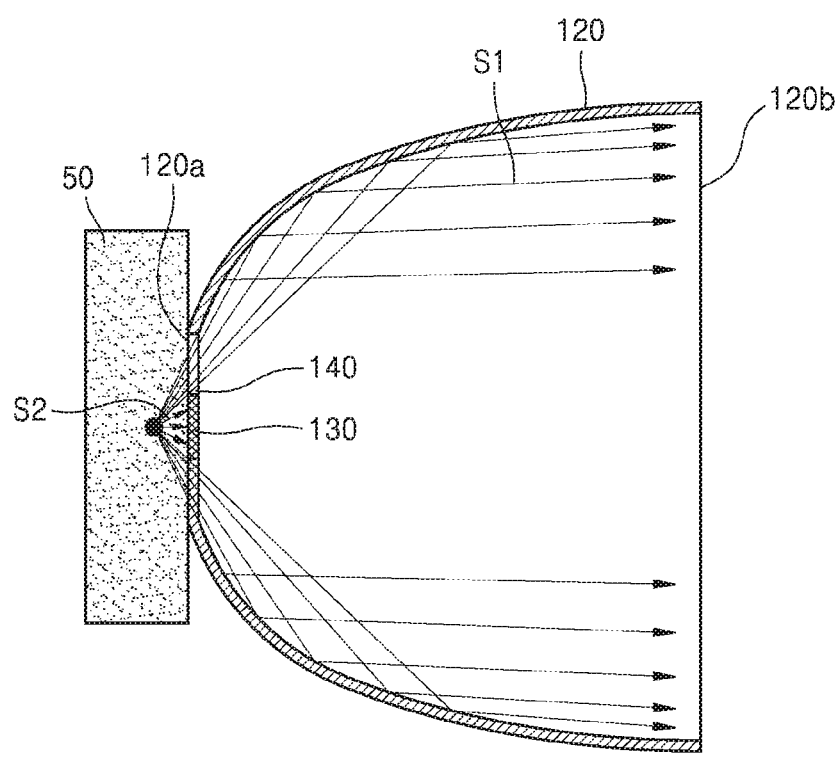
FIG. 12 is a view illustrating a propagation path of scattered light output from a target object in the Raman spectral system illustrated in FIG. 9.

FIG. 12 illustrates an example path along which scattered light output from the target object 50 propagates. Referring to FIG. 12, fluorescence signals S2 of scattered light output from the target object 50 toward the center portion of the entrance surface 120a of the non-imaging collection unit 120 are blocked by the Raman filter 130, and Raman signals S1 reaching a peripheral portion of the entrance surface 120a of the non-imaging collection unit 120 may pass through the transparent member 140 and enter the non-imaging collection unit 120. Then, the non-imaging collection unit 120 delivers the incident Raman signals S1 toward the exit surface 120b.

Since the target object 50 has turbidity, scattered light emitted from the target object 50 contains Raman signals S1 and also fluorescence signals S2 that hinder reception of the Raman signals S1. Since most of the fluorescence signals S2 are included in a center portion of the scattered light emitted from the target object 50, if the Raman filter 130 is provided on the center portion of the entrance surface 120a of the non-imaging collection unit 120, the fluorescence signals S2 may be reduced or blocked, and thus, only the Raman signals S1 may be collected in the non-imaging collection unit 120.

The angle of scattered light output from the target object 50 in response to incident light L is random, and thus the scattered light may be incident on the Raman filter 130 at angles other than the right angle. According to results of a simulation experiment, when a short pass filter transmitting only a wavelength of 790 nm was used as a Raman filter, and wavelengths ranging from about 800 nm to about 900 nm were incident on the Raman filter at angles of 30° and 60°, most of the wavelengths did not pass through the Raman filter. Therefore, all scattered light incident on the Raman filter 130 at oblique angles may be blocked.

The collection optics system including the non-imaging collection unit 120 and the Raman filter 130 may selectively collect only Raman signals S1 from scattered light output from the target object 50 and output the Raman signals S1 through the exit surface 120b. Then, the Raman signals S1 collected as described above may be received by the spectrometer 150 and analyzed. In this manner, reception of fluorescence signals S2 included in scattered light output from the target object 50 may be suppressed, and a Raman spectrum containing only Raman signals S1 may be obtained. Here, as an example, an on-chip spectrometer having a small size by integrating resonators or filters on a substrate may be used as the spectrometer 150.

As described above, the Raman spectral system 100 of the example embodiment may selectively collect only Raman signals S1 from scattered light output from the target object 50 while suppressing reception of fluorescence signals S2 from the scattered light by using the non-imaging collection unit 120 and the Raman filter 130. That is, when the target object 50 having turbidity similar to the human skin is irradiated with light L such as a laser beam, scattered light output from the target object 50 includes Raman signals S1 and fluorescence signals S2 as well, and most of the fluorescence signals S2 are included in a center portion of the scattered light. Therefore, the Raman filter 130 configured to reduce or block fluorescence signals S2 is provided on a portion of the entrance surface 120a of the non-imaging collection unit 120 corresponding to the center portion of scattered light, that is, on a center portion of the entrance surface 120a, such that the non-imaging collection unit 120 may selectively collect only the Raman signals S1. Therefore, for example, only Raman signals relating to blood glucose in the skin may be more effectively detected using the Raman spectral system 100. In addition, if an on-chip spectrometer is used as the spectrometer 150, the Raman spectral system 100 may have a smaller size.

The above description is given for the case of using a CPC as the non-imaging collection unit 120. However, example embodiments are not limited thereto. That is, examples of the non-imaging collection unit 120 may include various concentrators.

Figure 13A:
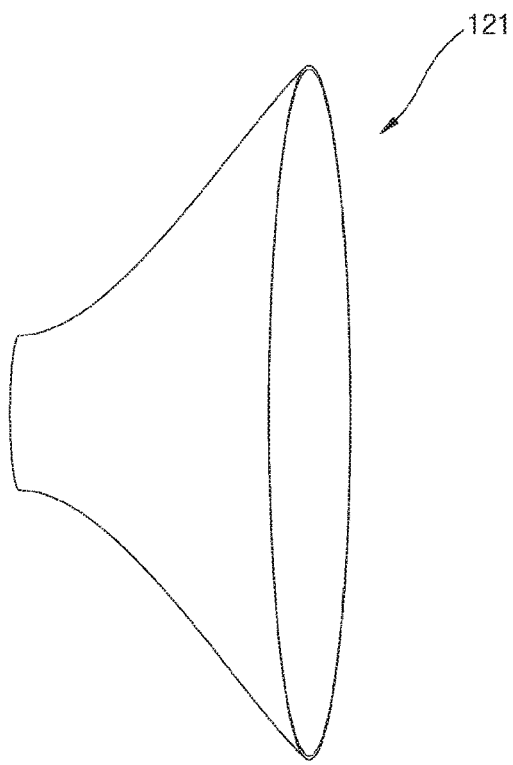
FIGS. 13A to 13D are illustrate examples of the non-imaging collection unit that are applicable to the Raman spectral system illustrated in FIG. 9.
Figure 13B:
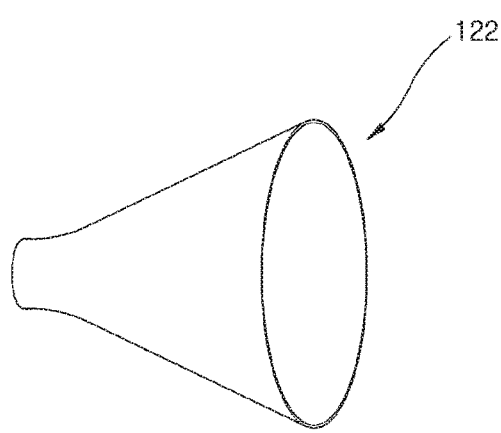
Figure 13C:
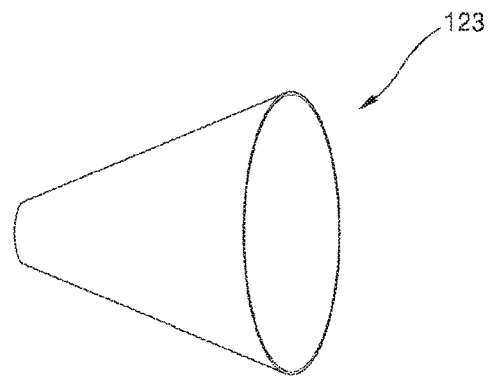
Figure 13D:
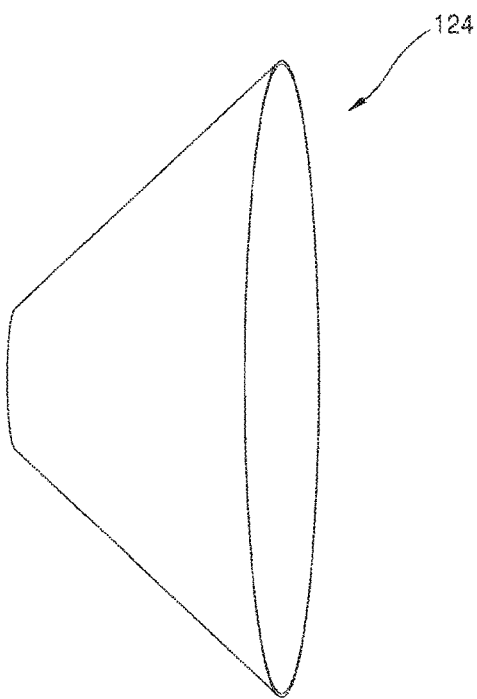

FIGS. 13A to 13D illustrate examples of the non-imaging collection unit 120 that are applicable to the Raman spectral system 100 shown in FIG. 9. FIG. 13A illustrates an elliptical hyperboloid concentrator (EHC) 121, and FIG. 13B illustrates a circular hyperboloid concentrator (CHC) 122. FIG. 13C illustrates a circular cone concentrator (CCC) 123, and FIG. 13D illustrates an elliptical cone concentrator (ECC) 124. The above-described concentrators are examples. That is, examples of the non-imaging collection unit 120 include other various concentrators.

In the above, the case in which the Raman filter 130 transmits incident light in only one wavelength band is described. However, example embodiments are not limited thereto. For example, the light source 110 may emit light in a plurality of wavelength bands, and a Raman filter configured to transmit light in the plurality of wavelength bands may be provided.

Figure 14A:
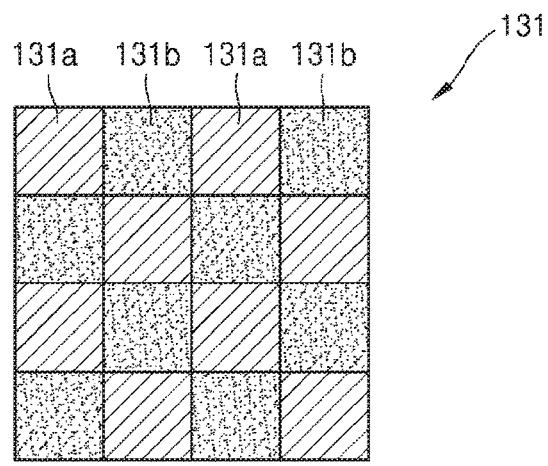
FIGS. 14A and 14B illustrate examples of a Raman filter that are applicable to the Raman spectral system illustrated in FIG. 9.
Figure 14B:
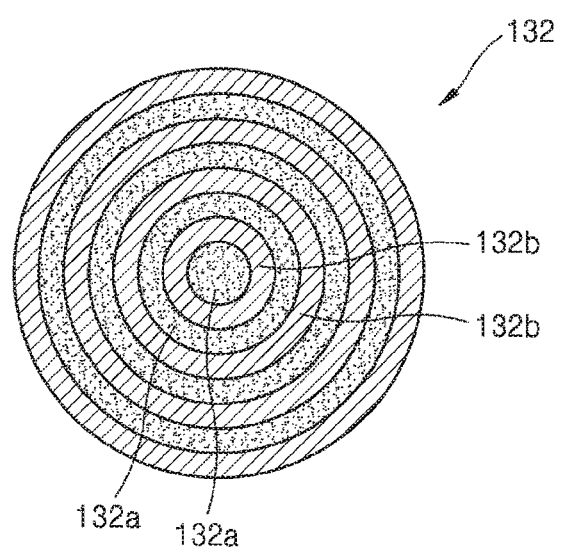

FIGS. 14A and 14B illustrate examples of the Raman filter 130 that are applicable to the Raman spectral system 100 shown in FIG. 9.

Referring to FIG. 14A, a tetragonal Raman filter 131 may be provided on the center portion of the entrance surface 120a of the non-imaging collection unit 120. The Raman filter 131 may include at least one first wavelength filter 131a and at least one second wavelength filter 131b. The first wavelength filter 131a may transmit incident light L in a first wavelength band, and the second wavelength filter 131b may transmit incident light L in a second wavelength band. The first and second wavelength filters 131a and 131b may each have a tetragonal shape and may be arranged in a grid form.

Referring to FIG. 14B, a circular Raman filter 132 may be provided on the center portion of the entrance surface 120a of the non-imaging collection unit 120. The Raman filter 132 may include at least one first wavelength filter 132a configured to transmit incident light L in a first wavelength band, and at least one second wavelength filter 132b configured to transmit incident light in a second wavelength band. The first and second wavelength filters 132a and 132b may be arranged as concentric rings.

Figure 15A:
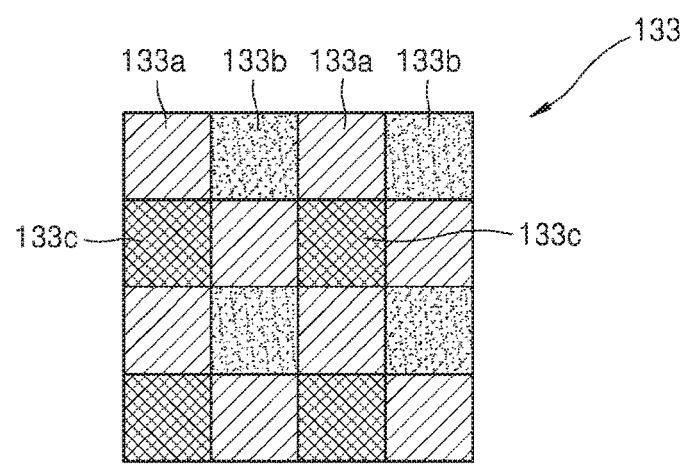
FIGS. 15A and 15B illustrate examples of the Raman filter that are applicable to the Raman spectral system illustrated in FIG. 9.
Figure 15B:
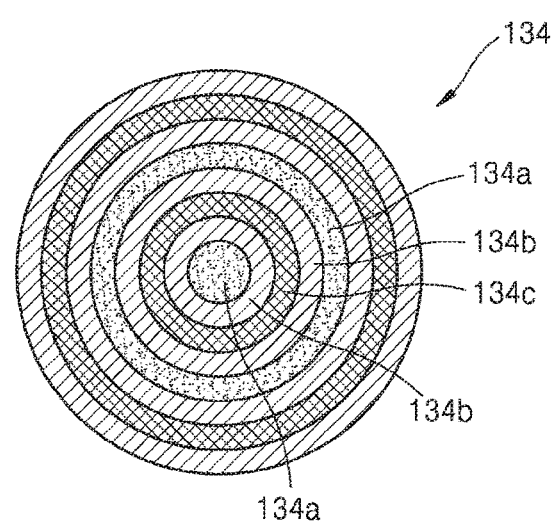

FIGS. 15A and 15B illustrate examples of the Raman filter 130 that are applicable to the Raman spectral system 100 shown in FIG. 9.

Referring to FIG. 15A, a tetragonal Raman filter 133 may include at least one first wavelength filter 133a, at least one second wavelength filter 133b, and at least one third wavelength filter 133c. The first wavelength filter 133a may transmit light in a first wavelength band, the second wavelength filter 133b may transmit light in a second wavelength band, and the third wavelength filter 133c may transmit light in a third wavelength band. Here, the first, second, and third wavelength filters 133a, 133b, and 133c may have a tetragonal shape and may be arranged in a grid form.

Referring to FIG. 15B, a circular Raman filter 134 may include at least one first wavelength filter 134a configured to transmit light in a first wavelength band, at least one second wavelength filter 134b configured to transmit light in a second wavelength band, and at least one third wavelength filter 134c configured to transmit light in a third wavelength band. The first, second, and third wavelength filters 134a, 134b, and 134c may be arranged as concentric rings.

In the above-described examples, the Raman filters 131, 132, 133, and 134 may be configured to transmit light in two or three wavelength bands. However, a Raman filter configured to transmit light in four or more wavelength bands may be implemented. In addition, although the Raman filters 131, 132, 133, and 134 have a tetragonal or circular shape in the above-described examples, the shape of the Raman filters 131, 132, 133, and 134 may be variously modified.

The Raman filters 131, 132, 133, and 134 configured to transmit light in a plurality of wavelength bands may be used for shifted excitation Raman difference spectroscopy (SERDS) and background subtraction. In addition, since the depth to which incident light penetrates the skin varies according to the wavelength of the light, the Raman filters 131, 132, 133, and 134 configured to transmit light in a plurality of wavelength bands may be used to obtain Raman information according to the depth of the skin.

Figure 16:
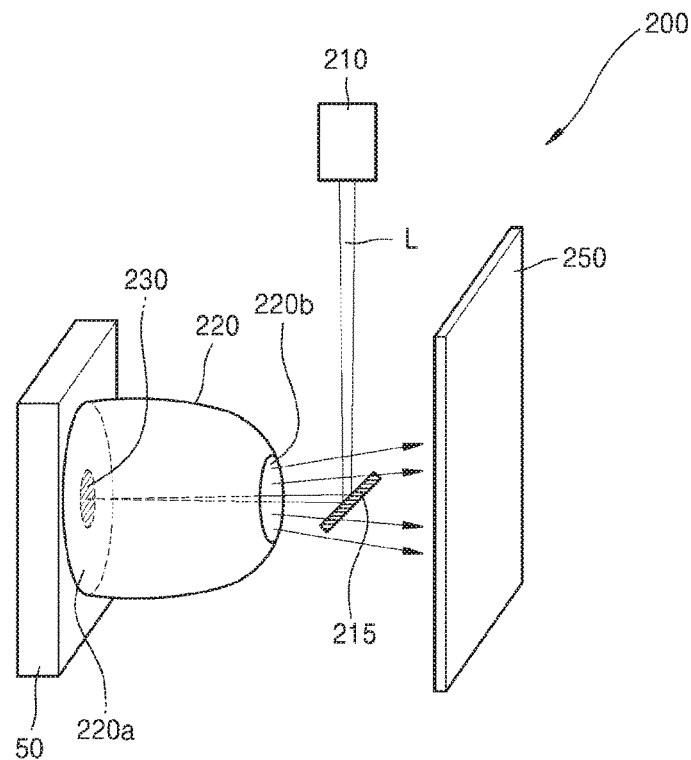
FIG. 16 is a perspective view illustrating a Raman spectral system according to an example embodiment.

FIG. 16 illustrates a Raman spectral system 200 according to an example embodiment.

Referring to FIG. 16, the Raman spectral system 200 may include a light source 210 configured to emit light L toward an target object 50, a collection optics system configured to selectively collect Raman signals from scattered light output from the target object 50, and a spectrometer 250 configured to receive the collected Raman signals from the collection optics system.

Light L emitted from the light source 210 may be reflected by a refection mirror 215 and may be incident on a test region of the target object 50 through a Raman filter 230. The collection optics system may selectively collect Raman signals from the scattered light output from the target object 50. The collection optics system may include a non-imaging collection unit 220 and the Raman filter 230. For example, the non-imaging collection unit 220 may include a CPC, an EHC, a CHC, a CCC, or an ECC. However, example embodiments of the non-imaging collection unit 220 are not limited thereto.

The non-imaging collection unit 220 may include an entrance surface 220a on which scattered light output from the target object 50 is incident, and an exit surface 120b located opposite the entrance surface 220a and through which Raman signals are output. In the example embodiment, the entrance surface 220a of the non-imaging collection unit 220 may have an area larger than that of the exit surface 220b.

The Raman filter 230 may be provided on a portion of the entrance surface 220a of the non-imaging collection unit 220 to block fluorescence signals. For example, the Raman filter 230 may be provided on a portion of the entrance surface 220a of the non-imaging collection unit 220 on which most fluorescence signals are incident. That is, the Raman filter 230 may be provided on a center portion of the entrance surface 220a. The Raman filter 230 may be configured to transmit light in one or a plurality of wavelength bands. In addition, a transparent member may be further provided on the entrance surface 220a of the non-imaging collection unit 220 in a region around the Raman filter 230. In addition, a band filter configured to transmit a particular Raman wavelength may be provided on the entrance surface 220a of the non-imaging collection unit 220 around the Raman filter 230.

The collection optics system including the non-imaging collection unit 220 and the Raman filter 230 may selectively collect only Raman signals from scattered light output from the target object 50. Then, the Raman signals collected as described above may be received by a spectrometer 250 such as an on-chip spectrometer and may be analyzed.

Figure 17:
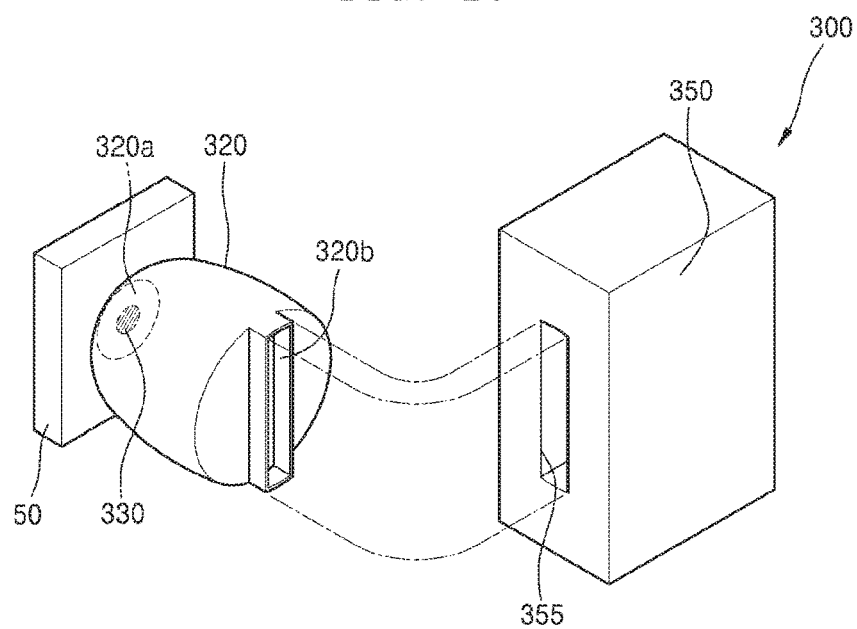
FIG. 17 is a perspective view illustrating a Raman spectral system according to an example embodiment.

FIG. 17 illustrates a Raman spectral system 300 according to an example embodiment.

Referring to FIG. 17, the Raman spectral system 300 may include a light source, a collection optics system configured to selectively collect Raman signals from scattered light output from a target object 50, and a spectrometer 350 configured to receive the collected Raman signals from the collection optics system. Here, the spectrometer 350 may be a general dispersive-type spectrometer having a slit 355.

The collection optics system may include a non-imaging collection unit 320 and a Raman filter 330. The non-imaging collection unit 320 may include an entrance surface 320a on which scattered light output from the target object 50 is incident, and an exit surface 320b located opposite the entrance surface 320a and through which Raman signals are output. In the example embodiment, the exit surface 320b of the non-imaging collection unit 320 may be inserted into the slit 355 of the spectrometer 350. Therefore, the exit surface 320b of the non-imaging collection unit 320 may have a shape corresponding to the slit 355 of the spectrometer 350.

The Raman filter 330 may be provided on a portion of the entrance surface 320a of the non-imaging collection unit 320 on which most fluorescence signals are incident. That is, the Raman filter 330 may be provided on a center portion of the entrance surface 320a. The Raman filter 330 may be configured to transmit light in one or a plurality of wavelength bands. The collection optics system including the non-imaging collection unit 320 and the Raman filter 330 may selectively collect only Raman signals from scattered light output from the target object 50, and the Raman signals may be received by the spectrometer 350 through the slit 355 and analyzed.

Figure 18:
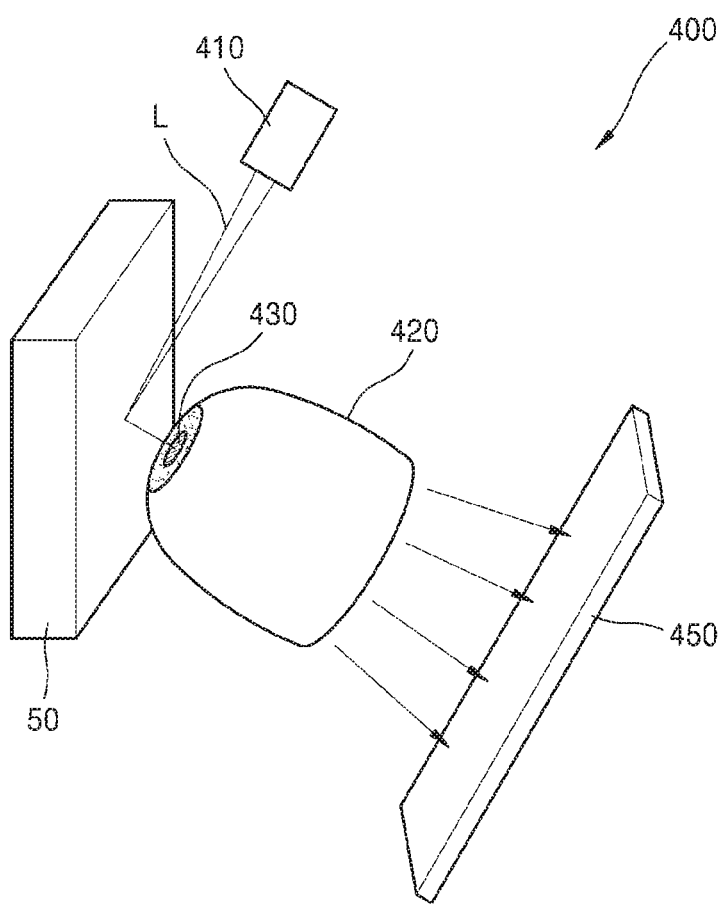
FIG. 18 is a perspective view illustrating a Raman spectral system according to an example embodiment.

FIG. 18 is a view illustrating a Raman spectral system 400 according to an example embodiment. Referring to FIG. 18, the Raman spectral system 400 may include a light source 410 configured to emit light L toward an target object 50, a collection optics system configured to selectively collect Raman signals from scattered light output from the target object 50, and a spectrometer 450 configured to receive the collected Raman signals from the collection optics system.

Light L emitted from the light source 410 may be incident on a surface of the target object 50 at an oblique angle. The collection optics system may selectively collect Raman signals from scattered light output from the target object 50. The collection optics system may include a non-imaging collection unit 420 and a Raman filter 430. For example, the non-imaging collection unit 420 may include a CPC, an EHC, a CHC, a CCC, or an ECC. However, example embodiments of the non-imaging collection unit 420 are not limited thereto.

The non-imaging collection unit 420 may include an entrance surface on which scattered light output from the target object 50 is incident, and an exit surface through which Raman signals are output. Here, the entrance surface of the non-imaging collection unit 420 may have an area smaller than the area of the exit surface of the non-imaging collection unit 420. Alternatively, the entrance surface of the non-imaging collection unit 420 may have an area larger than the area the exit surface of the non-imaging collection unit 420.

The Raman filter 430 may be provided on a portion of the entrance surface of the non-imaging collection unit 420 on which most fluorescence signals are incident. That is, the Raman filter 430 may be provided on a center portion of the entrance surface of the non-imaging collection unit 420. The Raman filter 430 may be configured to transmit light in one or a plurality of wavelength bands. The collection optics system including the non-imaging collection unit 420 and the Raman filter 430 may selectively collect only Raman signals from scattered light output from the target object 50. Then, the Raman signals collected as described above may be received by the spectrometer 450 and analyzed.

As described above, according to the one or more example embodiments, the non-imaging collection unit and the Raman filter may be used to reduce or suppress reception of fluorescence signals included in scattered light output from a target object and selectively collect only Raman signals from the scattered light. For example, when a target object having turbidity such as the human skin is irradiated with a laser beam, scattered light output from the target object includes Raman signals and also fluorescence signals that hinder reception of the Raman signals. Most of the fluorescence signals are included in a center portion of the scattered light. Therefore, the Raman filter configured to block fluorescence signals may be provided on a center portion of the entrance surface of the non-imaging collection unit corresponding the center portion of the scattered light, thereby suppressing reception of the fluorescence signals and selectively collecting only the Raman signals. The Raman spectral system may be used to more effectively detect Raman signals from blood glucose in the human skin. In addition, if an on-chip spectrometer is used, a smaller Raman spectral system may be implemented for use as a diagnosis sensor for mobile health.

In addition, a Raman spectral system including a Raman filter configured to transmit a plurality of wavelength bands may be provided for SERDS and background subtraction. In addition, since the depth to which light emitted from a light source penetrates the skin varies according to the wavelength of the light, a Raman filter configured to transmit light in a plurality of wavelength bands may be used to obtain Raman information according to the depth of the skin.

It should be understood that example embodiments described herein should be considered in a descriptive sense only and not for purposes of limitation. Descriptions of features or aspects within each example embodiment should be considered as available for other similar features or aspects in other example embodiments.

While one or more embodiments have been described with reference to the figures, it will be understood by those of ordinary skill in the art that various changes in form and details may be made therein without departing from the spirit of the disclosure, the scope of which is defined in the following claims and their equivalents.

What is claimed is:

1. A collection optics system for a spectrometer, the collection optics system being configured to selectively collect a Raman signal from scattered light output from a target object, the collection optics system comprising:
   a non-imaging collection unit configured to collect the Raman signal from the scattered light and output the Raman signal, the non-imaging collection unit comprising an entrance surface on which the scattered light is incident and an exit surface through which the Raman signal is output, the entrance surface being configured to he brought in contact with the target object; and
   a Raman filter provided on a portion of the entrance surface of the non-imaging collection unit and configured to block a portion of the scattered light comprising a fluorescence signal.

2. The collection optics system of claim 1, wherein the target object comprises a material having turbidity and outputs the scattered light comprising the fluorescence signal and the Raman signal based on light incident on the target object from a light source.

3. The collection optics system of claim 2, wherein the target object comprises human skin, and the Raman signal comprises a blood glucose Raman signal.

4. The collection optics system of claim 2, wherein the Raman filter is provided on a center portion of the entrance surface of the non-imaging collection unit, the center portion being a portion on which the fluorescence signal is incident.

5. The collection optics system of claim 4, wherein a size of the entrance surface of the non-imaging collection unit is equal to or less than 1 cm.

6. The collection optics system of claim 5, wherein a size of the Raman filter is equal to or less than 1 mm.

7. The collection optics system of claim 4, wherein the Raman filter is further configured to transmit the light incident on the target object in an incident-light wavelength band and configured to block the scattered light output from the target object in a scattered-light wavelength band.

8. The collection optics system of claim 7, wherein the Raman filter is further configured to transmit the light incident in a wavelength band.

9. The collection optics system of claim 7, wherein the Raman filter comprises a plurality of wavelength filters configured to transmit the light incident in a plurality of wavelength bands.

10. The collection optics system of claim 9, wherein the plurality of wavelength filters are provided in a grid form or concentric ring form.

11. The collection optics system of claim 4, wherein a transparent member configured to transmit the scattered light containing the Raman signal or a band filter configured to transmit a predetermined Raman wavelength is provided on the entrance surface of the non-imaging collection unit around the Raman filter.

12. The collection optics system of claim 1, wherein the non-imaging collection unit further comprises an elliptical hyperboloid concentrator, a circular hyperboloid concentrator, a circular cone concentrator, an elliptical cone concentrator, or a compound parabolic concentrator.

13. The collection optics system of claim 1, wherein an area of the entrance surface of the non-imaging collection unit is smaller than an area of the exit surface of the non-imaging collection unit.

14. The collection optics system of claim 1, wherein an area of the entrance surface of the non-imaging collection unit is larger than an area of the exit surface of the non-imaging collection unit.

15. A Raman spectral system comprising:
a light source configured to emit light to a target object;
a collection optics system configured to selectively collect a Raman signal from a scattered light output from the target object based on the light incident from the light source and output the Raman signal; and
a spectrometer configured to receive the Raman signal output from the collection optics system,
wherein the collection optics system comprises:
a non-imaging collection unit configured to collect the Raman signal from the scattered light and output the Raman signal, the non-imaging collection unit comprising an entrance surface on which the scattered light is incident and an exit surface through which the Raman signal is output, the entrance surface being configured to be brought in contact with the target object; and
a Raman filter provided on a portion of the entrance surface of the non-imaging collection unit and configured to block a portion of the scattered light comprising a fluorescence signal.

16. The Raman spectral system of claim 15, wherein the Raman filter is provided on a center portion of the entrance surface of the non-imaging collection unit, the center portion being a portion on which the fluorescence signal is incident.

17. The Raman spectral system of claim 16, wherein the Raman filter is further configured to transmit the light incident on the target object in an incident-light wavelength band and configured to block the scattered light output from the target object in a scattered-light wavelength band.

18. The Raman spectral system of claim 16, wherein a transparent member configured to transmit the scattered light comprising the Raman signal or a band filter configured to transmit a predetermined Raman wavelength is provided on the entrance surface of the non-imaging collection unit around the Raman filter.

19. The Raman spectral system of claim 15, wherein the non-imaging collection unit further comprises an elliptical hyperboloid concentrator, a circular hyperboloid concentrator, a circular cone concentrator, an elliptical cone concentrator, or a compound parabolic concentrator.

20. The Raman spectral system of claim 15, wherein the light emitted from the light source is incident on a surface of the target object at right angle or an oblique angle.

21. The Raman spectral system of claim 15, wherein the spectrometer comprises an on-chip spectrometer.

22. The Raman spectral system of claim 15, wherein the spectrometer comprises a dispersive-type spectrometer comprising a slit configured to receive the Raman signal, and
wherein the exit surface of the non-imaging collection unit is inserted in the slit.

* * * * *